US00PP09013P

United States Patent [19]

Warner

[11] Patent Number: Plant 9,013

[45] Date of Patent: Dec. 13, 1994

[54] CLIMBING MINIATURE ROSE PLANT NAMED CHEWALLOP

[75] Inventor: Christopher H. Warner, Shropshire, England

[73] Assignee: Bear Creek Gardens, Inc., Medford, Oreg.

[21] Appl. No.: 201,237

[22] Filed: Feb. 24, 1994

[51] Int. Cl.[5] ..... A01H 5/00

[52] U.S. Cl. ..... Plt./4

[58] Field of Search ..... Plt. 2, 4, 6, 10.1

*Primary Examiner*—Howard J. Locker

*Attorney, Agent, or Firm*—Klarquist Sparkman Campbell Leigh & Whinston

[57] ABSTRACT

A climbing miniature rose plant having an upright climbing habit of growth; small, glossy, dark green foliage; resistance to powdery mildew and rust; and ability to flower from early until late in the growing season.

1 Drawing Sheet

The present invention relates to a new and distinct variety of rose plant of the climbing miniature class which was originated by me by crossing an unnamed seedling from a cross of the variety MACel with an unnamed seedling resulting from a cross of the varieties MACba and "Sutter's Gold" (U.S. Plant Pat. No. 885) with the variety HARpiccolo.

The primary objective of this breeding was to produce a new rose variety having the climbing habit of the female parent combined with the repeat flowering and small foliage of the male parent. The objective was substantially achieved, along with other desirable improvements, as evidenced by the following unique combination of characteristics that are outstanding in the new variety and that distinguish it from its parents, as well as from all other varieties of which I am aware:

1. Small, glossy foliage covering the whole plant;
2. Flowering from early to late in the season over the whole plant;
3. Upright climbing habit of growth; and
4. Resistance to powdery mildew and rust.

Asexual reproduction of this new variety by budding and by softwood cuttings as performed at Wasco, Calif., and Newport, Shropshire, England, shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—MACel × (MACba × "Sutter's Gold" [U.S. Plant Pat. No. 885]).

*Pollen parent.*—HARpiccolo.

Classification:

*Botanical.*—*Rose hybrida.*

*Commercial.*—Climbing miniature.

FLOWER

Observations made from specimens grown in a garden environment at Somis, Calif., and Newport, Shropshire, England.

Blooming habit: Recurrent.

Bud:

*Size.*—13 mm long when the petals start to unfurl.

*Form.*—The bud form is short, pointed ovoid.

*Color.*—When sepals first divide, bud color is Orange Group 33C. When half blown, the upper side of the petals are Orange Group 33A, and the lower side of the petals are Orange Group 33C.

*Sepals.*—Color: Green Group 138B. Surface texture: Covered in fine hairs. There are three lightly appendaged sepals and two unappendaged sepals with hairy edges.

*Receptacle.*—Color: Green Group 137B. Shape: Funnel. Size: Small (3 mm by 3 mm). Surface: Smooth.

*Peduncle.*—Length: Short (19 to 25 mm). Surface: Glandular. Color: Medium green and bronzy. Strength: Stiff, erect, slender.

Bloom:

*Size.*—Small. Average open size is 25 to 38 mm.

*Borne.*—Several together, in pyramidal clusters of 5 to 10 flowers.

*Stems.*—Long (75 to 91 cm); strong.

*Form.*—When first open: High centered. Permanence: All petals curl, quill fashion.

*Petalage.*—Number of petals under normal conditions: 20.

*Color.*—The upper side of the petals are Orange-Red Group 33A. The reverse side of the petals are Orange-Red Group 33C. The base of each petal is Yellow-Orange Group 15B. The major color on the upper side is Orange-Red Group 33A.

*Variegations.*—None.

*Discoloration.*—The general tonality at the end of the first day: No change. At the end of the third day: No change.

*Fragrance.*—Slight.

Petals:

*Texture.*—Thick.

*Shape.*—Deltoid.

*Form.*—Edges slightly quilled.

*Arrangement.*—Imbricated, with few petaloids in the center.

*Persistence.*—Drop off cleanly.

*Lastingness.*—On the plant: Fair (5 days). As a cut flower: Fair (5 to 6 days).

Reproductive parts:

*Anthers.*—Size: Medium. Quantity: Many. Color: Yellow. Arrangement: Regular around styles.

*Filaments.*—Color: Yellow.

*Pollen.*—Color: Gold yellow.

*Styles.*—Color: Red.

*Stigmas.*—Color: Greenish white.

Form: Climber.

Growth: Very vigorous, upright, branching. Will grow to 2.5 meters the first year in California. Foliage: Number of leaflets on normal mid-stem leaves: 5.

*Size.*—Small (76 mm×51 mm).

*Quantity.*—Abundant.

*Color.*—New foliage: Reddish (Greyed Purple 183A). Old foliage: Dark green (Green Group 135A).

Leaflets:

*Shape.*—Pointed oval.

*Texture.*—Upper side: Leathery, glossy.

*Edge.*—Smooth.

*Serration.*—Single, small.

*Petiole rachis.*—Color: Green.

*Petiole underside.*—Smooth, with occasional prickles.

*Stipules.*—Short, bearded.

*Disease resistance.*—Resistant to mildew and rust under normal growing conditions at Somis, Calif.

Wood:

*New wood.*—Color: Reddish. Bark: Smooth.

*Old wood.*—Color: Green. Bark: Smooth.

Prickles:

*Quantity.*—On main canes from base: Ordinary. On laterals from main canes: Ordinary.

*Form.*—Hooked downward.

*Color when young.*—Red.

Small prickles:

*Quantity.*—On main stalks: None. On laterals: None.

I claim:

1. A new and distinct variety of rose plant of the climbing miniature class, substantially as herein shown and described, characterized particularly as to novelty by the unique combination of its upright climbing habit of growth; small, glossy, dark green foliage; resistance to powdery mildew and rust; and ability to flower from early until late in the growing season.

* * * * *

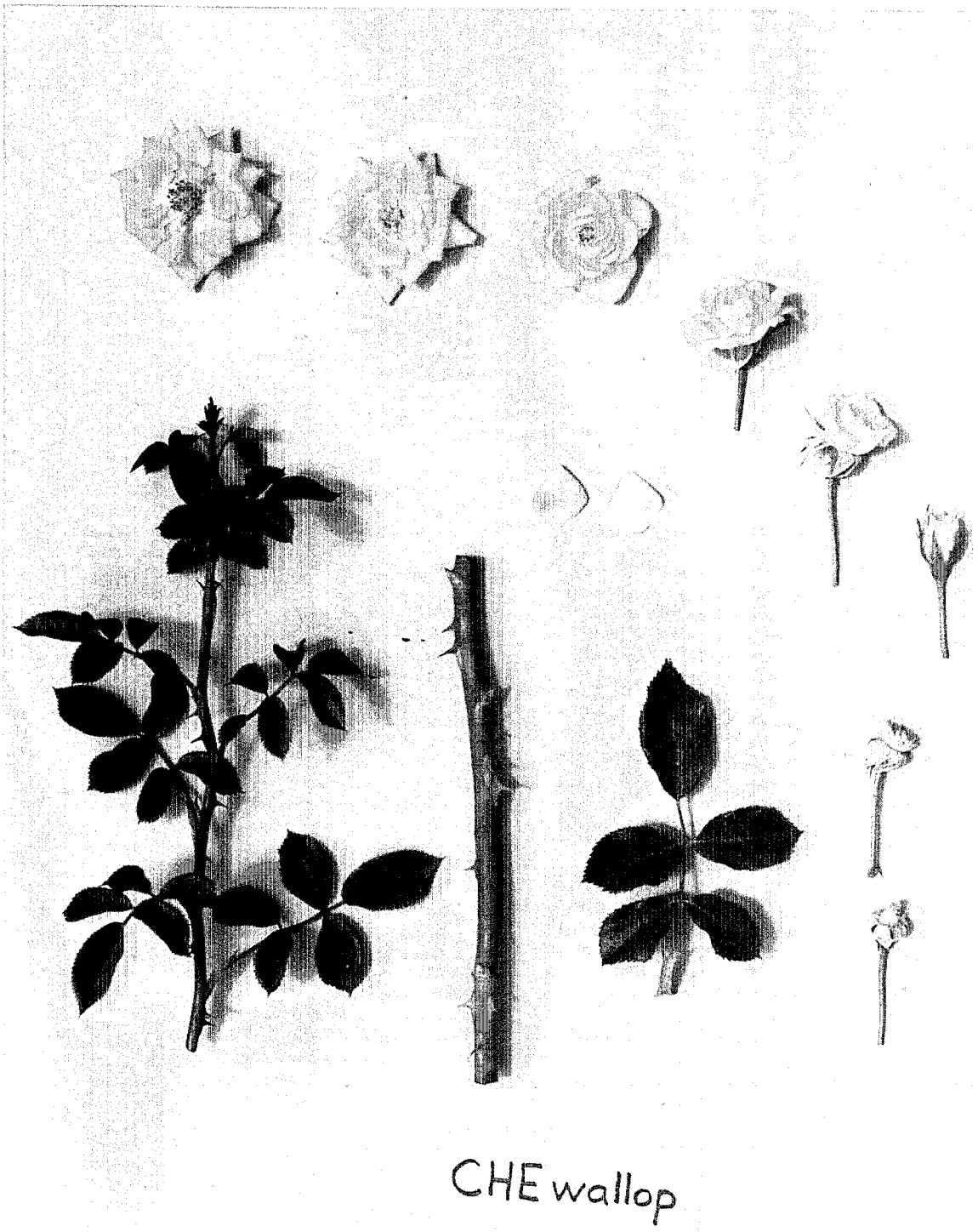
CHEwallop